US010877011B2

(12) United States Patent
Cummings et al.

(10) Patent No.: US 10,877,011 B2
(45) Date of Patent: Dec. 29, 2020

(54) SYSTEMS AND METHODS FOR MONITORING FOR A GAS ANALYTE

(71) Applicant: Nexceris, LLC, Lewis Center, OH (US)

(72) Inventors: Stephen Randall Cummings, Worthington, OH (US); Scott Lawrence Swartz, Columbus, OH (US); Nicholas Brannigan Frank, Columbus, OH (US); William John Dawson, Dublin, OH (US); Davion Matthew Hill, Grandview Heights, OH (US); Benjamin H. Gully, Oslo (NO)

(73) Assignee: NEXCERIS, LLC, Lewis Center, OH (US)

( * ) Notice: Subject to any disclaimer, the term of this patent is extended or adjusted under 35 U.S.C. 154(b) by 414 days.

(21) Appl. No.: 15/637,381

(22) Filed: Jun. 29, 2017

(65) Prior Publication Data
US 2018/0003685 A1    Jan. 4, 2018

Related U.S. Application Data

(60) Provisional application No. 62/356,111, filed on Jun. 29, 2016, provisional application No. 62/454,516, filed on Feb. 3, 2017.

(51) Int. Cl.
*G01N 33/00*    (2006.01)
*G01N 27/04*    (2006.01)
(Continued)

(52) U.S. Cl.
CPC ......... *G01N 33/0063* (2013.01); *G01N 27/04* (2013.01); *H01M 10/4228* (2013.01); *H01M 10/0525* (2013.01)

(58) Field of Classification Search
None
See application file for complete search history.

(56) References Cited

U.S. PATENT DOCUMENTS 6,155,160 A    12/2000  Hochbrueckner
6,204,769 B1 *  3/2001  Arai ..................... B60L 3/0046
                                                      340/632
(Continued)

FOREIGN PATENT DOCUMENTS

CN    204650704 U    9/2015
CN    206012357 U    3/2017
(Continued)

OTHER PUBLICATIONS

Davion Hill, Sensor Enhanced and Model Validated Life, Extension of Li-Ion Batteries for Energy Storage, Jul. 1, 2015, 28 pages. (Year: 2015).*

(Continued)

*Primary Examiner* — Tung S Lau
(74) *Attorney, Agent, or Firm* — Benesch, Friedlander, Coplan & Aronoff LLP

(57) ABSTRACT

Systems and methods are described herein for monitoring a gas source for a gas analyte. The gas source can be monitored for release of the gas analyte, for example, during a given gas source state. A sensor signal can be generated characterizing an amount of the gas analyte being released by the gas source. The gas sensor signal can be evaluated relative to a threshold. An alert signal can be generated based on a result of the comparison to provide a warning that unwanted and/or hazardous amounts of gas is being released by the gas source.

26 Claims, 10 Drawing Sheets

(51) Int. Cl.
*H01M 10/42* (2006.01)
*H01M 10/0525* (2010.01)

(56) References Cited

U.S. PATENT DOCUMENTS

| | | | |
|---|---|---|---|
| 7,326,931 B2 | 2/2008 | Frodl et al. | |
| 2001/0016278 A1 | 8/2001 | Onishi et al. | |
| 2002/0154019 A1* | 10/2002 | Kimoto | G01N 33/0037 340/632 |
| 2005/0200475 A1* | 9/2005 | Chen | G08B 29/24 340/521 |
| 2007/0008104 A1* | 1/2007 | McBain | G08B 23/00 340/517 |
| 2007/0141404 A1 | 6/2007 | Skidmore et al. | |
| 2007/0229294 A1 | 10/2007 | Vossmeyer et al. | |
| 2009/0121592 A1* | 5/2009 | De Nando | A61M 16/01 312/209 |
| 2010/0094565 A1 | 4/2010 | Prince et al. | |
| 2011/0059341 A1* | 3/2011 | Matsumoto | H01M 10/613 429/82 |
| 2012/0328233 A1* | 12/2012 | Chakravarty | G01N 21/552 385/12 |
| 2014/0216129 A1 | 8/2014 | Schmidlin et al. | |
| 2014/0295218 A1 | 10/2014 | Hakansson et al. | |
| 2015/0350799 A1* | 12/2015 | Schnaare | G08B 21/182 381/56 |
| 2016/0133995 A1 | 5/2016 | Hattori et al. | |
| 2016/0197382 A1* | 7/2016 | Sood | G01N 29/26 429/92 |

FOREIGN PATENT DOCUMENTS

| | | |
|---|---|---|
| CN | 107478995 A | 12/2017 |
| CN | 108695568 A | 10/2018 |
| CN | 102967542 B | 5/2019 |
| EP | 3214429 A4 | 11/2017 |
| EP | 3479434 A2 | 5/2019 |
| JP | 2002289265 A | 10/2002 |
| JP | 2018018815 A | 2/2018 |
| KR | 20180017958 A | 2/2018 |
| RU | 2531883 C2 | 10/2014 |
| WO | 2014133677 A1 | 9/2014 |

OTHER PUBLICATIONS

David Rosewater, Analyzing system safety in lithium-ion grid energy storage, 12 pages (Year: 2015).*
Celina Mikolajczak, Lithium-Ion Batteries Hazard and Use Assessment, 126 pages (Year: 2011).*
Safety of lithium-ion batteries, 26 pages (Year: 2013).*
International Search Report and Written Opinion issued in PCT application PCT/US2017/043603, dated Dec. 20, 2017.
International Preliminary Report on Patentability issued in PCT application PCT/US2017/043603, dated Jan. 1, 2019.
Hill et al., "Detection of Off Gassing from Li-ion Batteries", IEEE EnergyTech 2013, May 21-23, 2013.
Communication pursuant to Rule 164(1) EPC, issued in European application No. 17821451.6 dated Mar. 17, 2020.
Extended European Search Report, issued in European application No. 17821451.6 dated Jun. 26, 2020.

* cited by examiner

SYSTEMS AND METHODS FOR MONITORING FOR A GAS ANALYTE

CROSS REFERENCED TO RELATED APPLICATION

This application claims the benefit of U.S. Provisional Application No. 62/356,111 filed on Jun. 29, 2016, entitled "SYSTEMS AND METHODS FOR ANALYTE DETECTION AND CONTROL", and U.S. Provisional Application No. 62/454,516 filed on Feb. 3, 2017, entitled "SYSTEMS INCLUDING AN ENERGY STORAGE ENCLOSURE AND MONITORING THEREOF", the contents of both are herein incorporated by reference.

GOVERNMENT LICENSE RIGHTS

A part of this invention was made with government support under Department of the Navy contract number N00024-15-C-4002. The government has certain rights in the invention.

TECHNICAL FIELD

This disclosure generally relates to systems and methods for monitoring for a gas analyte.

BACKGROUND

In many applications, the potential for unwanted and/or hazardous gases to be emitted into a surrounding environment exists. The ability to react quickly to developing dangers resulting from these gases is of need since it is known that particular gases can have an impact on a surrounding environment and human life. The impact can be devastating and can lead to system failures, mechanical failures, plant failures, devices failures, explosions, fires, and in some instances death.

Batteries are known to contribute to the dangers that hazardous gases can have on the surrounding environment. For example, when a battery begins to degrade, the battery can become susceptible to a condition known as "thermal runaway". If left unchecked, this condition can cause the battery to leak and/or explode. Thermal runaway can be initiated by a short circuit within a battery (e.g., a cell of the battery), improper battery use, physical abuse, manufacturing defects, or exposure of the battery to extreme external temperatures. Thermal runaway occurs when an internal reaction rate of the battery increases to a point that more heat can be generated than can be withdrawn, leading to a further increase in both the internal reaction rate and heat generated.

The effects of a thermal runaway condition can depend on battery type. For example, in flooded electrolyte batteries, such as lead acid batteries, the thermal runaway condition can cause hydrogen to be released, resulting in a hazardous gas escaping into a surrounding environment. In sealed batteries, such as pouched lithium ion batteries, which can be used in devices, such as laptops, cell phones, and the like, the thermal runaway condition can cause an expansion, which can result in the sealed battery exploding and releasing the hazardous electrolyte gas into the surrounding environment.

SUMMARY

In one example, a method can include monitoring a gas source for a gas analyte. The method can further include generating a sensor signal characterizing an amount of the gas analyte being released by the gas source. The method can further include receiving the sensor signal and evaluating the sensor signal relative to a threshold. The method can further include generating an alert signal based on a result of the evaluation.

In another example, a system can include an enclosure housing a gas source, and a monitoring system. The monitoring system can include a gas sensor that can be located within the enclosure and can be configured to monitor for a gas analyte released by the gas source. The monitoring system can further include a non-transitory memory to store machine readable instructions, and a processor to access the memory and execute the machine readable instructions. The machine readable instructions can cause the processor to receive a sensor signal generated by the gas sensor characterizing an amount of the gas analyte being released by the gas source, evaluate the sensor signal relative to a threshold, and generate an alert signal based on a result of the evaluation.

In an even further example, a method can include monitoring a gas source for release of a gas analyte and generating a first sensor signal characterizing an amount of the gas analyte being released by the gas source. The method can further include monitoring an ambient environment for ambient gas and generating a second sensor signal characterizing an amount of the ambient gas present in the ambient atmosphere. The method can further include determining a first sensor output based upon a percent change of the first sensor signal relative to a first averaged sensor signal and determining a second sensor output based upon a percent change of the second sensor signal relative to a second averaged sensor signal. The method can further include evaluating the first sensor output relative to the second sensor output and generating an alert signal based on a result of the evaluation.

In another example, a system can include an enclosure housing a gas source, and a monitoring system. The monitoring system can include a first gas sensor that can be located within the enclosure and can be configured to monitor for a gas analyte released by the gas source. The monitoring system can further include a second gas sensor located within the enclosure and that can be configured to monitor an ambient environment for ambient gas. The monitoring system can further include a non-transitory memory to store machine readable instructions, and a processor to access the memory and execute the machine readable instructions. The machine readable instructions can cause the processor to receive a first sensor signal characterizing an amount of the gas analyte being released by the gas source and receive a second sensor signal characterizing an amount of the ambient gas present in the ambient atmosphere. The machine-readable instructions can further cause the processor to determine a first sensor output based upon a percent change of the first sensor signal relative to a first averaged sensor signal and determine a second sensor output based upon a percent change of the second sensor signal relative to a second averaged sensor signal. The machine-readable instructions can further cause the processor to evaluate the first sensor output relative to the second sensor output and generate an alert signal based on a result of the evaluation.

DETAILED DESCRIPTION

Figure 1:
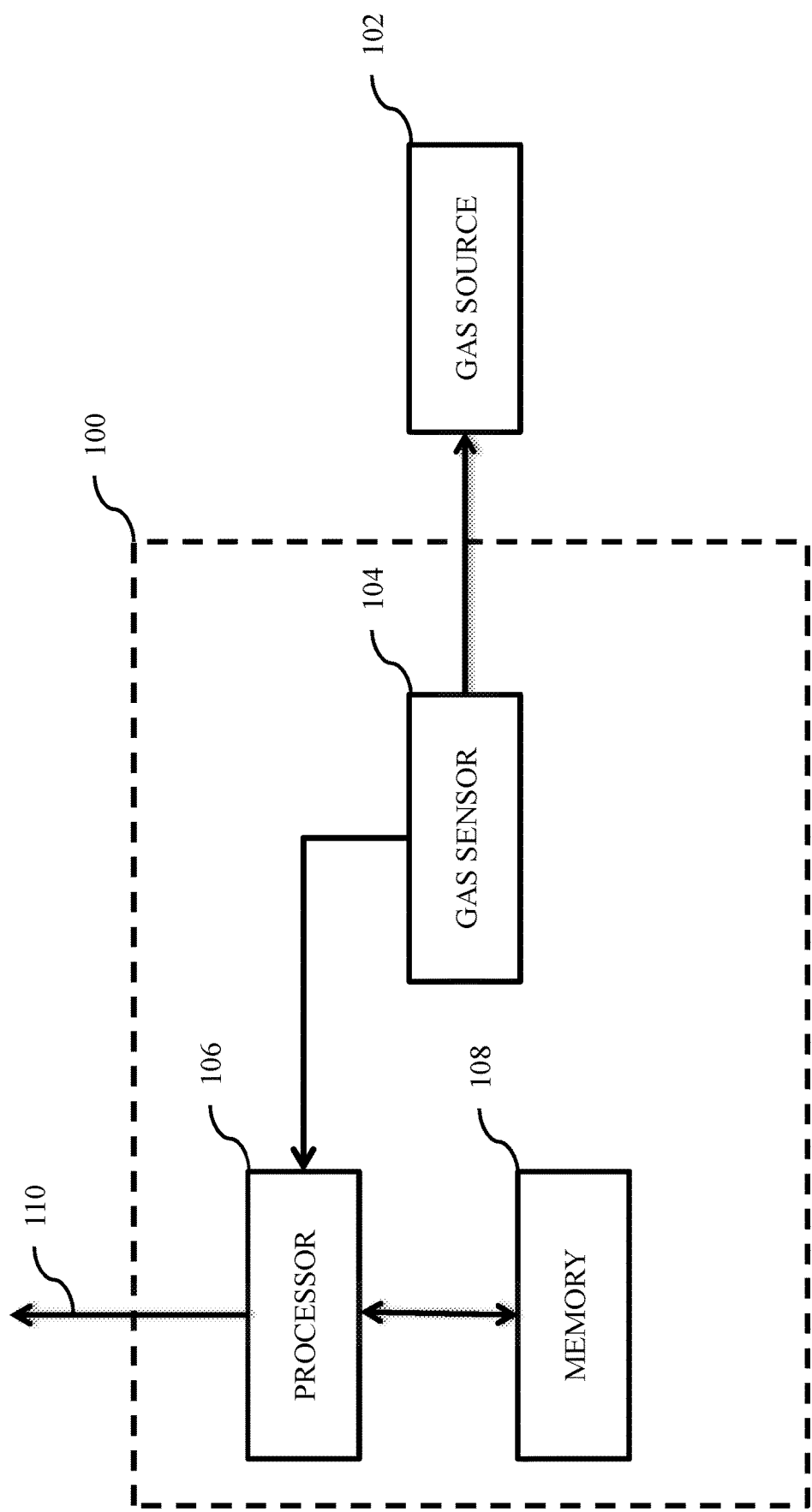
FIG. 1 depicts an example of a gas analyte monitoring system.

This disclosure generally relates to systems and methods for monitoring for a gas analyte. In some examples, the gas source can include a battery and the gas analyte is an off-gas. Thus, the systems and methods described herein can monitor for battery off-gas. Although, examples are described herein relating to monitoring a battery off-gas condition, it should be appreciated that the systems and methods described herein can be implemented in any environment that includes a gas source. For example, the environment can include, but not limited, a safety environment, a test environment, such as a laboratory, a storage environment, such as a data center, an industrial environment, such as a combustion system, a commercial environment, a residential environment, a military environment, a transportation environment, such as a vehicle, a product, such as a commercial and residential device and/or apparatus, or like environments. Accordingly, the scope of this disclosure should not be limited by the specific examples described herein.

The term "gas analyte" as used herein can refer to a gas released by and/or generated by a gas source. Thus, the term "gas analyte" can include, a leaked gas, an off-gas, a gas by-product of a chemical reaction, or the like. A gas analyte can include an electrolyte gas, such as a volatile electrolyte solvent, a volatile component of an electrolyte mixture of the battery, or the like. Volatile electrolyte species can include diethyl carbonate, dimethyl carbonate, methyl ethyl carbonate, ethylene carbonate, propylene carbonate, vinylene carbonate or the like. Additionally, the gas analyte can include a lithium-ion battery off gas, carbon dioxide, carbon monoxide, methane, ethane, hydrogen, oxygen, nitrogen oxides, volatile organic compounds, hydrogen sulfide, sulfur oxides, ammonia, chlorine, propane, ozone, ethanol, hydrocarbons, hydrogen cyanide, combustible gases, flammable gases, toxic gases, corrosive gases, oxidizing gases, reducing gases, or the like.

In an example, the gas source can include the battery. The systems and methods described herein can be implemented to monitor the battery for a gas analyte. Over their lifespan, batteries can degrade progressively, which can result in a reduced capacity, cycle life, and safety. A degrading battery can release a gas, which can be referred to herein as the "gas analyte". The gas analyte can be released by the battery during a cycling condition, such as a charge cycle or a discharge cycle. One or more causes of battery degradation can include improper battery use, physical abuse, manufacturing defects, exposure of the battery to extreme external temperatures, overcharge, or the like. The systems and methods described herein can detect the gas analyte during the cycle condition to provide an early warning of a thermal runaway condition. In one example, the early warning can include an audible alarm, a visual alarm, fire suppression, communication with other systems and a user. The gas analyte detected during the cycle condition can be interpreted as a warning that the battery can be at risk of thermal runaway. By providing an early warning, fires, explosions and injuries that can be caused in response to a thermal runaway condition can be substantially mitigated.

Furthermore, by providing an early warning, operational limits of the battery can be substantially extended, and enable monetization of high value, but otherwise "abusive" services, such as occasional high-power discharges or low depths of discharge. Additionally, life extension beyond an industry-standard 80% capacity is possible. The systems and methods described herein can provide substantial benefits, such as improved control and reduction in an overall battery system cost. Moreover, the systems and methods described herein can be configured to monitor any type of battery gas analyte. Thus, the systems and methods described herein can be used to monitor a lithium ion battery, a lead-acid battery, or the like.

The systems and methods described herein can be configured with a plurality of enclosures, such as battery enclosures. Thus, the systems and methods described herein can be used to monitor for a gas analyte released by one or more batteries located within a battery enclosure. The term "battery enclosure" as used herein refers to any housing that can partially encapsulate the one or more batteries. In an example, the enclosure can include a ventilated enclosure or a non-ventilated enclosure. The ventilated enclosure can include a ventilation system that can include an intake and an exhaust. In an even further example, the enclosure can include a battery storage cabinet, a shipping container or a battery rack.

Furthermore, the term "processor" as used herein can refer to any device capable of executing machine readable instructions, such as a computer, controller, an integrated circuit (IC), a microchip, or any other device capable of implementing logic. The term "memory" as used herein can refer to a non-transitory computer storage medium, such as volatile memory (e.g., random access memory), non-volatile memory (e.g., a hard disk drive, a solid-state drive, flash memory or the like) or a combination thereof.

Although examples are described herein relating to a semiconductor gas sensor, it should be appreciated that any type of gas sensor can be used, such as a chemi-resisitive sensor, an electrochemical sensor, a semi conductive metal-oxide sensor, a catalytic sensor, a thermal conductivity sensor, a metal-oxide semiconductor, a potentiometric sensor, an optical sensor, an infrared (IR) sensor, an amperometric sensor, or the like. In a non-limiting example, a hydrogen sensor, such as NTM SenseH$_2$® or NTM SenseH$_2$®-R sensor offered by Nexceris, LLC can be used.

Moreover, although gas sensor examples are described herein, it should be appreciated that other sensors can be used. Thus, it should be appreciated that the systems and methods described herein are equally applicable to other types of monitoring applications other than gas monitoring. These sensors can include a temperature sensor, a pressure sensor, a proximity sensor, an altitude sensor, a humidity sensor, a radiation sensor, a smoke sensor, a conductivity sensor, a pH sensor, an accelerometer, a speed sensor, a radar, a Doppler radar, a level sensor, a sonar sensor, a lambda sensor, or the like. As an example, the systems and methods described herein can monitor for a change in an environmental condition (e.g., temperature, pressure, proximity, altitude, humidity, radiation, smoke, conductivity, pH, acceleration, speed, distance, velocity, motion, level, such as a liquid, oxygen level, or the like), generate a sensor signal characterizing the change in the environment condition, receive the sensor signal (e.g., at a processor), evaluate the sensor signal relative to a threshold, and generate an alert signal based on a result of the evaluation. Accordingly, the systems and methods described herein can have a wide range of applicability beyond that of gas monitoring.

FIG. 1 illustrates an example of a monitoring system 100 that can be configured to monitor a gas source 102 for a gas analyte. In an example, the gas source 102 can include a battery. The system 100 can include a gas sensor 104. The gas sensor 104 can be positioned relative to the gas source 102 such that the gas sensor 104 is within a gas analyte sensing range of the gas source 102. For example, if the gas source 102 is located within an enclosure (or another system) (not depicted in FIG. 1), the gas sensor 104 can be positioned within the enclosure (or other system) and within the gas analyte sensing range of the gas source 102. In another example, the enclosure can be a sealed battery enclosure such that the battery is sealed off from a surrounding environment. The gas sensor 104 can be configured to monitor the gas source 102 for a gas analyte. The gas analyte within the gas source 102 can be related to a state of the gas source 102 wherein the gas source 102 can be releasing the gas analyte.

The gas sensor 104 can include a semiconductor gas sensor. In one example, the gas sensor 104 can be a semiconductor gas sensor. The semiconductor gas sensor can include a common material. The common material can include tin dioxide, or the like. An electrical resistance of the common material can decrease when a gas, measured in parts-per-million (ppm), comes into contact with the common material. In some examples, the electrical resistance of the common material can increase when the gas comes into contact with the common material. The gas sensor 104 can include one or more additional components (not depicted in FIG. 1) that can be configured to detect the change in the electrical resistance in the common material and generate a signal representative of a given amount of the gas.

The gas sensor 104 can be configured to generate a sensor signal characterizing an amount of the gas analyte released by the gas source 102. The sensor signal can be generated based on a given electrical resistance of the common material. For example, during one or more battery states of the battery, the gas sensor 104 can be configured to generate one or more sensor signals characterizing amounts of the gas analyte released by the battery. The one or more battery states can include a charging state and a discharging state. A healthy battery can release substantially no gas analyte while charging and/or discharging. As the health of the battery can begin to degrade over time, the battery can release gaseous species corresponding to the gas analyte while charging and/or discharging.

The system 100 can further include a processor 106. The processor 106 can include memory 108 for storing data and machine-readable instructions. Alternatively, the memory 108 can be external to the processor 106, as shown in FIG. 1. The processor 106 can be configured to access the memory 108 and execute the machine-readable instructions stored in the memory 108. In one example, the processor 106 can be configured to access the memory 108 and execute the machine-readable instructions to perform one or more methods, as described herein. For example, the processor 106 can be configured to receive the one or more sensor signals characterizing amounts of the gas analyte released by the gas source 102. The processor 106 can further be configured to analyze the one or more sensor signals according to one or more threshold levels (bands). The one or more bands can be used to provide a determination of when a sensor signal generated by the gas sensor 104 has changed by a meaningful amount over a known baseline for the monitoring system 100. The known baseline can be a function of the one or more sensor signals generated by the gas sensor 104, for example, during a given gas source state of the gas source 102.

The one or more bands can include an N-sample moving average (MA), wherein N is an integer greater than one, an upper band at K times an N-sample standard deviation above the moving average (MA+K$\alpha$), wherein K is a number greater than one, and a lower band at K times an N-sample standard deviation below the moving average (MA−K$\alpha$). The N-sample MA can be calculated by summing the N-samples, and dividing the sum by N. In one example, the K and N parameters can be user definable parameters. The K parameter can correspond to a volatility factor. The parameter "$\alpha$" can correspond to the N-sample standard deviation of the one or more sensor signals.

In one example, the K and N parameters can be set to compensate for noise in a given sensor signal generated by the gas sensor 104. The processor 106 can be configured to differentiate noise from an actionable event as described herein. An actionable event can include, an audible alarm, a visual alarm, fire suppression, communication with another system, such as a safety system, or the like. In an even further example, the K and N parameters can be set to compensate for external factors, such as, temperature variations, humidity variations, both, or the like, which can introduce an error in the given sensor signal. Additionally or alternatively, the K and N parameters can be set to compensate for errors in the given sensor signal that can be caused by physical characteristics of the gas sensor 104. For example, the K and N parameters can be set to compensate for gas sensor drift. The K and N parameters can be adjusted during an operating life of the gas sensor 104 such that changes in the physical characteristics of the gas sensor 104 that can cause drift to be introduced into the given sensor signal can be substantially mitigated. Accordingly, drift errors in the given sensor signal generated by the gas sensor 104 can be substantially mitigated by adjusting the K and N parameters.

A gas analyte baseline for the system 100 can be defined. The gas analyte baseline can characterize an amount of the gas analyte released by the gas source 102 over a period of time. The period of time can be related to one or more gas source states associated with the gas source 102. The one or more gas source states can include an emitting gas state and a non-emitting gas state. Thus, in the emitting gas state, the source 102 can be releasing the gas analyte. In the example of the battery, while the battery is in the healthy state, a battery gas analyte baseline for the system 100 can be defined to characterize an amount of the gas analyte released by the battery during a cycle condition. A health battery can release substantially no gas analyte.

The gas sensor 104 can be configured to generate one or more baseline sensor signals. The processor 106 can further be configured to apply a MA to the one or more baseline sensor signals to determine a MA threshold. The MA of the one or more baseline sensor signals can be calculated by summing the one or more baseline sensor signals and dividing the sum by N, wherein N is a number of the one or more baseline sensor signals. The processor 106 can further be configured to determine an upper band threshold at K times a standard deviation of the one or more baseline sensor signals above the MA threshold. The processor 106 can further be configured to determine a lower band threshold at K times the standard deviation of the one or more baseline sensor signals below the MA threshold.

Additionally or alternatively, the processor 106 can be configured to determine a sensitivity threshold to compensate for a false-positive event that can be caused by the N-sample standard deviation having a value substantially equal to zero (e.g., within a given percentage range and/or value range of zero). For example, when the N-sample standard deviation is substantially zero, the monitoring system 100 can generate a false response. A false-positive event can include one or more events that can cause the gas sensor 104 to generate a non-gas analyte related response (e.g., a response that is not based on the gas analyte released by the gas source 102). Additional, as described herein, a false-positive event can include an event that can cause a gas sensor to generate a signal response based on one or more gases (or analytes) other than those released by a corresponding gas source. The sensitivity threshold can be a function of the MA and a difference value between a minimum sensitivity MS and a reference. For example, the sensitivity threshold can be defined by the following equation: $MA*(1-MS)$. The minimum sensitivity MS can be user definable.

The processor 106 can further be configured to compare the sensitivity threshold relative to one of the upper band threshold and the lower band threshold to identify a threshold that has a greatest value. The threshold with the greatest value can be used as an alert threshold as described herein. A given alert threshold can be established that can be sufficiently separated from the MA threshold by comparing the sensitivity threshold relative to a band threshold. When the N-sample standard deviation has a value substantially equal to zero, a corresponding threshold can be substantially near the MA threshold, which can result in the false-positive event. However, by comparing the sensitivity threshold relative to the band threshold, the false-positive event can be substantially mitigated, for example, by providing sufficient separation between the MA threshold and the alert threshold.

The processor 106 can further be configured to monitor for the gas analyte during the emitting gas state of the gas source 102 and generate a monitored sensor signal characterizing an amount of the gas analyte released by the gas source 102 at an instant of time. In the example of the battery, as the health of the battery can begin to degrade, the battery can release the gas analyte. The gas analyte can be detected during a cycle condition and can be interpreted as a warning that the battery is at risk of thermal runaway. The gas sensor 104 can be configured to monitor for the gas analyte during the cycle condition and generate a monitored sensor signal characterizing an amount of the gas analyte released by the battery at an instant of time. The processor 106 can further be configured to receive the monitored sensor signal. The processor 106 can further be configured to compare the monitored sensor signal relative to an alert threshold. The processor 106 can further be configured to generate an alert signal 110 based on a result of the comparison.

For example, the processor 106 can be configured to compare the monitored sensor signal relative to one of the sensitivity threshold and the lower band threshold. The processor 106 can be configured to generate the alert signal 110 in response to the monitored sensor signal being equal to or less than the one of the sensitivity threshold and the lower band threshold. Alternatively, the processor 106 can be configured to compare the monitored sensor signal relative to one of the sensitivity threshold and the upper band threshold. The processor 106 can be configured to generate the alert signal 110 in response to the monitored sensor signal being equal to or greater than one of the sensitivity threshold and the upper band threshold.

The processor 106 can further be configured to monitor for the gas analyte during the emitting gas state of the gas source 102 and generate a plurality of monitored sensor signals characterizing an amount of the gas analyte released by the gas source 102 over a corresponding period of time. The processor 106 can be configured to evaluate the plurality of monitored sensors signals to determine a number of the plurality of monitored sensor signals that is below a buffer threshold. The buffer threshold can compensate for a false-positive event in the monitoring system 100. The buffer threshold can correspond to a value identifying a number of monitored sensor signals needed for generation of an alert signal. The processor 106 can be configured to compare a most recent monitored sensor signal of the plurality of monitored sensor signals relative to the alert threshold and generate the alert signal 110 based on a result of the comparison, as described herein.

The processor 106 can further be configured to update the alert threshold based on the monitored sensor signals over time. The processor 106 can be configured to hold (e.g., latch) a given monitored sensor signal as an alert threshold in response to the given monitored sensor signal crossing a current alert threshold. Thus, the processor 106 can stop the MA calculation and update the alert threshold. The processor 106 can further be configured to compare the given monitored sensor relative to the updated alert threshold and generate the alert signal 110 based on a result of the comparison, as described herein.

The processor 106 can further be configured to transmit the alert signal 110 to one or more systems to cause the one or more systems to take one or more preemptive measures. The one or more preemptive measures can include automatic shutdown (e.g., a system, a device, a battery, etc.), initiation of fire extinguisher controls, an audible alarm, a maintenance warning, a text message, e-mail, or the like. In the example of the battery, the gas analyte detected during the cycle condition can be interpreted as a warning that the battery can be at risk of thermal runaway. By providing an early warning, fires, explosions and injuries that can be caused in response to a thermal runaway condition can be substantially mitigated. Thus, the monitoring system 100 can detect a thermal runaway condition in a development stage. Accordingly, by detecting a thermal runaway scenario at the development stage, preventive measures can be implemented to prevent hazardous conditions and damage to the battery.

Figure 2:
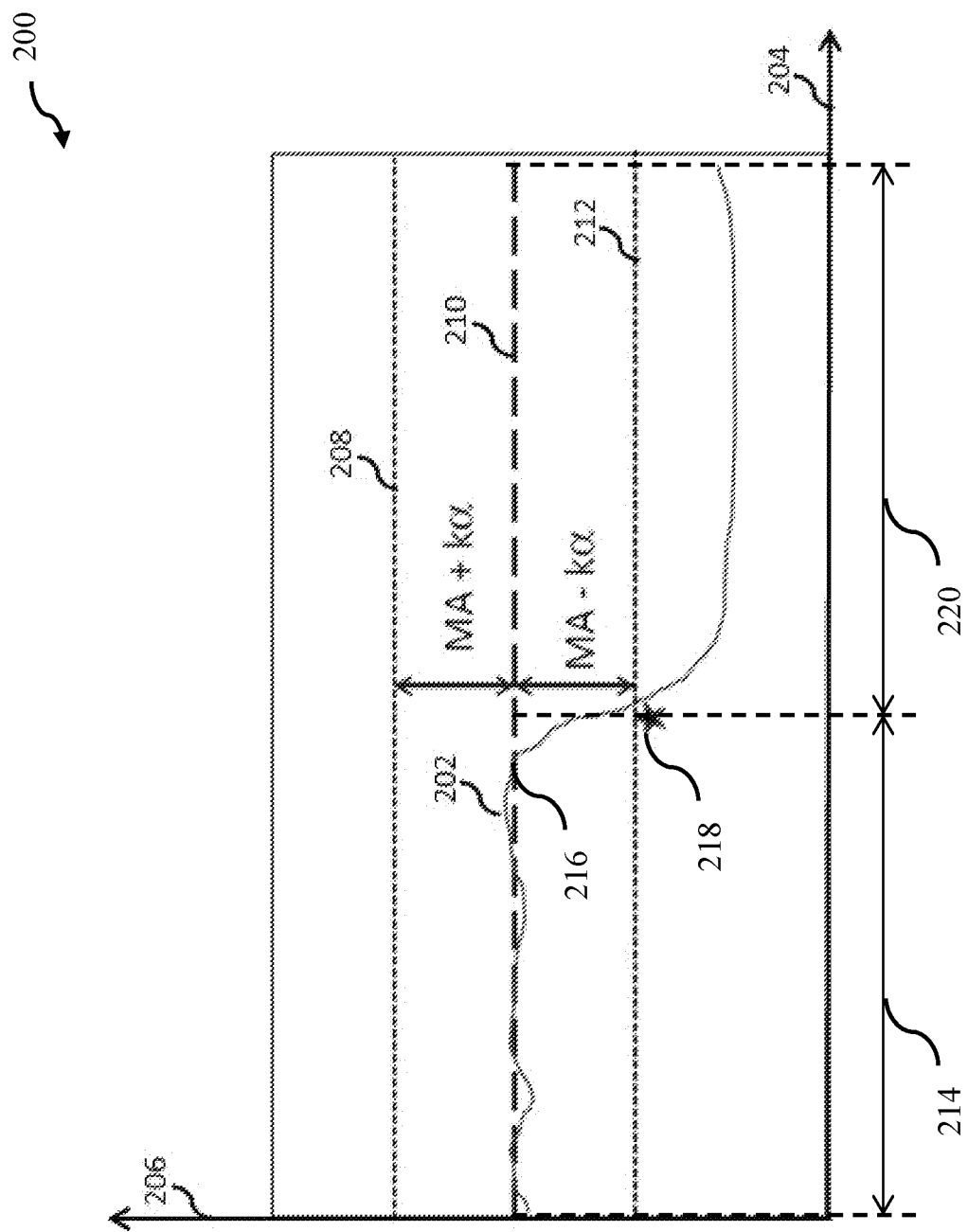
FIG. 2 depicts an example of a graph demonstrating gas analyte generated sensor signals plotted as a function of time.

FIG. 2 depicts an example of a graph 200 demonstrating gas analyte generated sensor signal 202 plotted as a function of time. The sensor signal 202 can be generated by a gas sensor (e.g., the gas sensor 104, as depicted in FIG. 1) that can be configured to monitor a gas source (e.g., the gas source 102) for a gas analyte condition. The graph 200 can include a horizontal axis 204 and a vertical axis 206. The horizontal axis 204 can correspond to time and can be referred to herein as a time axis 206. The vertical axis 206 can correspond to magnitudes of the sensor signal generated by the gas sensor over time, and can be referred to herein as a magnitude axis 206. A first magnitude 208 of the magnitude axis 206 can correspond to an upper band threshold, a second magnitude 210 of the magnitude axis 206 can correspond to a MA threshold and a third magnitude 212 of the magnitude axis 206 can correspond to a lower band threshold. In alternative example, the third magnitude 212 can correspond to the sensitivity threshold, the first magnitude 208 can correspond to the upper band threshold and second magnitude 210 can correspond to the MA threshold.

The graph 200 can further include a first range 214. The first range 214 can represent a period of time over the time axis 206 that the gas source is in a given state, such as a non-emitting gas state. In the example of the battery, the first range 214 can represent a period of time over the time axis 206 during which the battery can be in a healthy state, and thus can be releasing substantially no gas analyte. As depicted in FIG. 2, over the first range 214, the sensor signal 202 generated by the gas sensor can be substantially near the second magnitude 210 of the magnitude axis 206. The graph 200 can further include a transition event 216. The transition event 216 corresponds to an instance of time at which the gas source can be transitioning to another state, such as an emitting gas state. Thus at the transition event, the gas source can be releasing the gas analyte. In the example of the battery, the transition event corresponds to an instance of time at which the battery can begin to release the gas analyte. As more gas analyte is released by the gas source over the first range 214, the sensor signal 202 generated by the gas sensor based on an amount of the gas analyte released by the gas source can begin to decrease toward the third magnitude 212 of the magnitude axis 206, as depicted in FIG. 2.

At an alert event 218 of the graph 200, the magnitude of the sensor signal 202 can be substantially equal to the third magnitude 212. The alert event 216 can correspond to a point in time at which the gas source can be emitting a substantial amount of the gas analyte. A substantial amount of the gas analyte can be referred to herein as an undesired amount of the gas analyte and/or hazardous amount of the gas analyte. In the example of the battery, the alert event 218 can correspond to a point in time which the battery can be emitting a substantial amount of the gas analyte. This can be interpreted as a thermal runaway risk. During the alert event 216, an alert (e.g., the alert signal 110, as depicted in FIG. 1) can be generated (e.g., by the processor 106, as depicted in FIG. 1) to provide an early warning that unwanted and/or hazardous amounts of gas is being released by the gas source. In the example of the battery, the alert can provide early warning that the battery is at risk for thermal runaway.

The graph 200 can further include a second range 220. The second range 220 can represent a period of time over the time axis 206 that the gas source is in the other state, such as the emitting gas state. In the second range 220, one or more hazardous risks can develop, which if left unchecked can result in damage to a surrounding environment and/or the gas source. By providing an early warning at the alert event 216, preemptive actions can be taken to mitigate the one or more hazardous risks. In the example of the battery, the second range 220 can represent a period of time over the time axis 206 during which the battery is in a degraded state. If the battery is continued to be operated in the degraded state, the battery can experience thermal runaway, which can lead to damage to the battery or a surrounding external environment. By providing the early warning at the alert event 216 thermal runaway preemptive actions as described herein can be taken to avoid the risk for thermal runaway.

Figure 3:
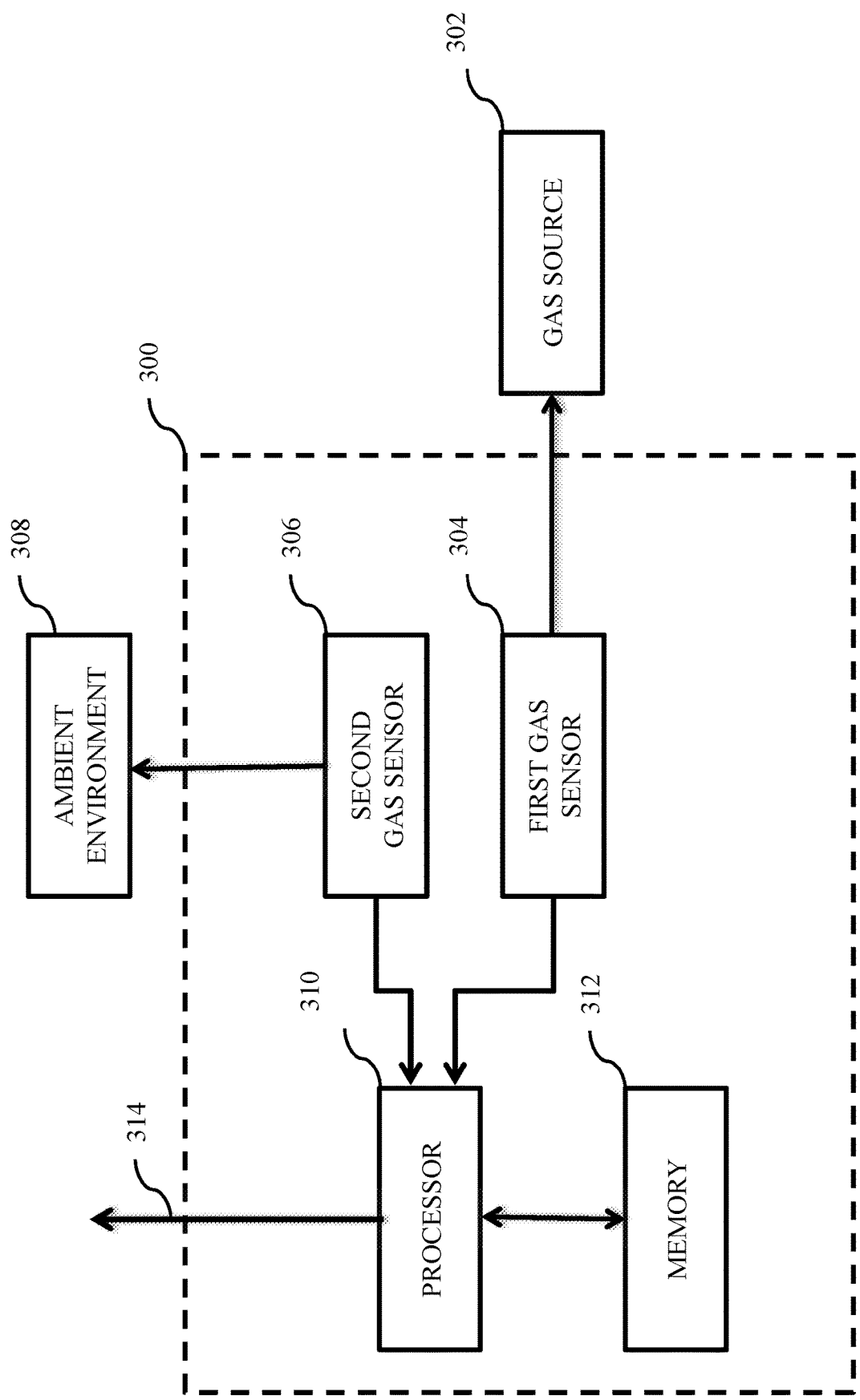
FIG. 3 depicts an example of another gas analyte monitoring system.

FIG. 3 illustrates an example of a monitoring system 300 that can be configured to monitor a gas source 302 for a gas analyte. In an example, the gas source 302 can include a battery. The system 300 can include a first gas sensor 304. The first gas sensor 304 can be positioned relative to the gas source 302, such that the first gas sensor 304 is within gas sensing range of the gas source 302. The first gas sensor 304 can be configured to monitor the gas source 302 for a gas analyte condition. The gas analyte condition can be related to a state of the gas source 302 wherein the gas source 302 can be releasing the gas analyte. The system 300 can further include a second gas sensor 306. In an example, the first and second gas sensors 304 and 306 can correspond to semiconductor gas sensors, such as the gas sensor 104, as depicted in FIG. 1.

The second gas sensor 306 can be configured to monitor for an ambient gas, for example, in an ambient environment 308. The term "ambient environment" as used herein can refer to an area of space that can remain substantially free of the gas analyte released by the gas source 302 during one or more gas source states of the gas source 302. The one or more gas source states can include an emitting gas state and a non-emitting gas state. The term "ambient gas" as used herein refers to any gas (or analyte) that can cause sensor signal responses in the first and second gas sensors 304 and 306. In an example, the ambient gas can include paint and fuel vapors. The second gas sensor 306 can be positioned relative to the gas source 302, such that the second gas sensor 306 is not within gas analyte sensing range of the gas source 302. Thus, the second gas sensor 306 can be substantially free of susceptibility to the gas analyte released by the gas source 302. Such an arrangement of the first and second gas sensors 304 and 306 can substantially mitigates false-positive events in the monitoring system 300, as will be described in greater detail herein.

The first gas sensor 304 can be configured to generate a first sensor signal characterizing an amount of the gas analyte released by the gas source 102. The first sensor signal can be generated based on a given electrical resistance of the common material of the first gas sensor 304. The first gas sensor 304 can be configured to generate a plurality of first sensor signals characterizing amounts of the gas analyte during the one or more gas source states of the gas source 302 over a period of time. For example, during a charging cycle and/or discharging cycle, a healthy battery can release substantially no gas analyte. As the health of the battery can begin to degrade, the battery can release gaseous species corresponding to the gas analyte during the charging cycle and/or discharging cycle.

The second gas sensor 304 can be configured to generate a second sensor signal characterizing an amount of an ambient gas in the ambient environment 308. The second sensor signal can be generated based on a given electrical resistance of a common material of the second gas sensor 304. The second gas sensor 304 can be configured to generate a plurality of second sensor signals characterizing amounts of the ambient gas in the ambient environment during the one or more gas source states of the gas source 302 over the period of time.

Figure 5:
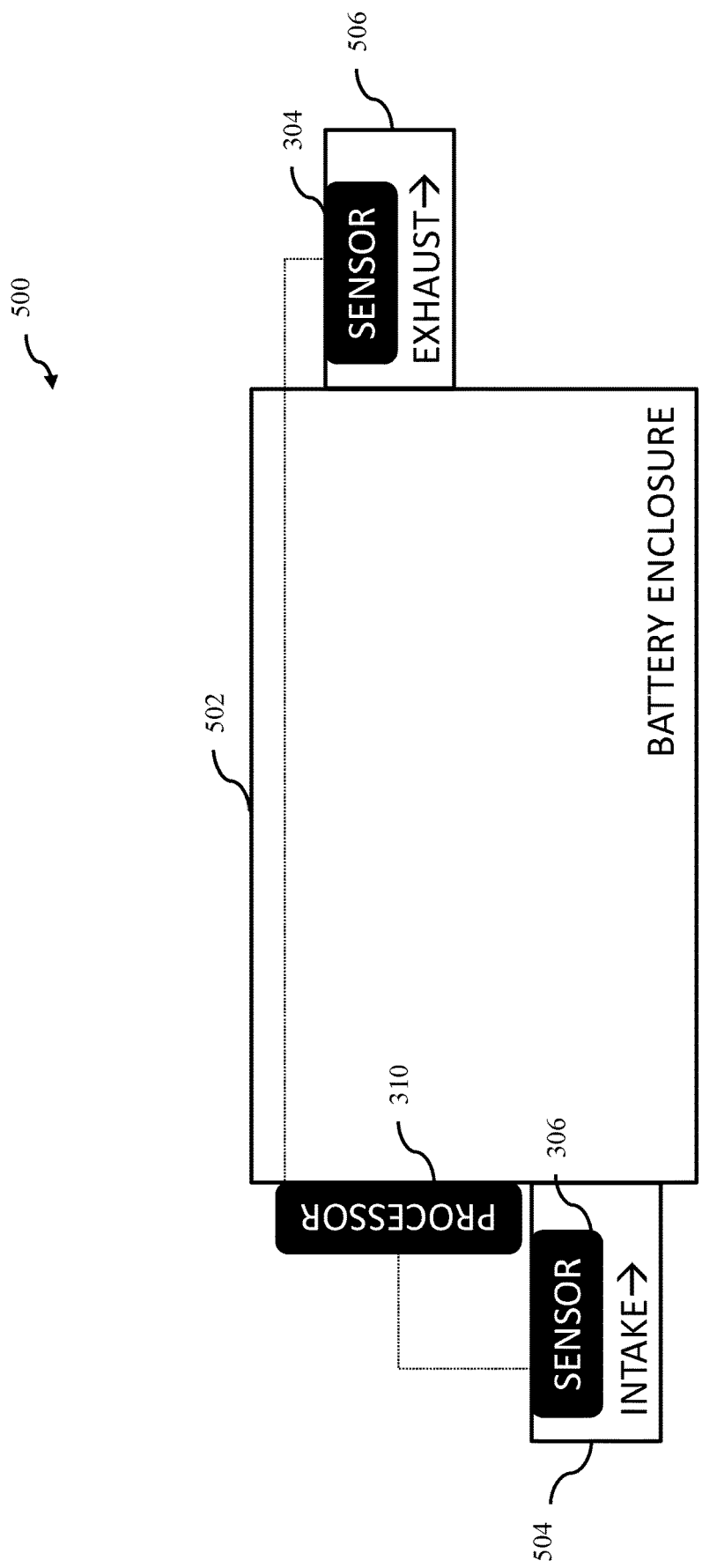
FIG. 5 depicts an even further example of an enclosure.
Figure 6:
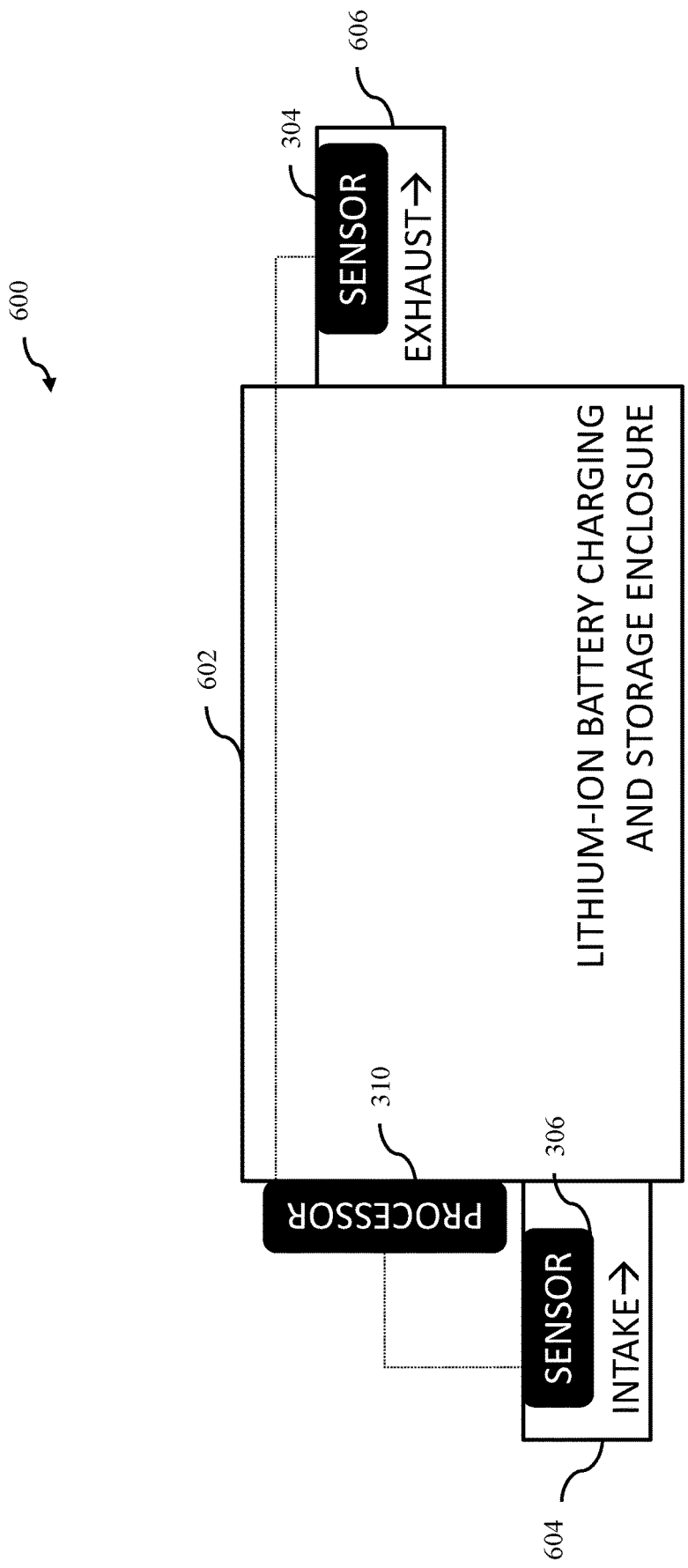
FIG. 6 depicts another example of an enclosure.

In one example, the battery can be located within a housing of a ventilated enclosure (e.g., a battery enclosure 502, as depicted in FIG. 5, or a battery enclosure 602, as depicted in FIG. 6). The first gas sensor 304 can be located down-stream in the ventilated enclosure along the gas path relative to the battery (e.g., at an exhaust of the ventilated battery enclosure, such as an exhaust 506, as depicted in FIG. 5 or exhaust 606, as depicted in FIG. 6). The second gas sensor 304 can be located up-stream in the ventilated enclosure along a gas path relative to the battery (e.g., at an intake of the ventilated battery enclosure, such as an intake 504, as depicted in FIG. 5, or an intake 604, as depicted in FIG. 6).

In the ventilated enclosure, to remove heat generated by the battery, the intake can be configured to draw ambient air in the ambient environment 308, which can include the ambient gas, and stream the ambient air down the gas path to the exhaust, which can be configured to expel the gas. As the ambient air is being streamed down the gas path along which the battery can be located, the heat generated by battery can be substantially removed to reduce an operating temperature of the battery. By positioning the first gas sensor 304 down-stream relative to the battery, the first gas sensor 304 can detect the gas analyte released by the battery when the gas analyte flows down the gas path, and is within sensing range of the first gas sensor 304. However, since the first gas sensor 304 is positioned down-stream, the ambient gas drawn by the intake can cause the first gas sensor 304 to generate a sensor response.

The one or more methods described herein can substantially mitigate the monitoring systems 300 susceptibility to the ambient gas based on sensor signals generated by both the first and second gas sensors 304 and 306. Thus, the one or methods described herein can reduce false-positive events in the monitoring system 300, and thereby false warnings of thermal runaway conditions. A false-positive event can include one or more events that can cause the first gas sensor 304 to generate the first sensor signal in response to gases (or analytes) other than those released by the gas source 302. In the example of the battery, false-positive events can cause the first gas sensor 304 to generate false responses, which can result in a false alert that the battery is at risk for thermal runaway. A false alert can result in thermal runway preventive measures to be implemented even though the battery could be not at risk of thermal runaway.

The monitoring system 300 can further include a processor 310. The processor 310 can include memory 312 for storing data and machine-readable instructions. Alternatively, the memory 312 can be external to the processor 310, as shown in FIG. 3. The processor 310 can be configured to access the memory 312 and execute the machine-readable instructions stored in the memory 312.

In one example, the processor 310 can be configured to access the memory 312 and execute the machine-readable instructions to perform the one or more methods described herein. The processor 310 can be configured to perform one or more methods that can compensate for effects that false-positive events can have on the monitoring system 300. Thus, susceptibility of the monitoring system 300 to generating a false alert that the battery is at risk for thermal runaway can be substantially mitigated. Accordingly, the monitoring system 300 as described herein can be employed in open-battery environments, such as ventilated enclosures.

To compensate for the effects of false-positive events, the processor 310 can be configured to establish a baseline reference for the monitoring system 300 to compensate for any part-to-part variability between sensor signals generated by the first gas sensor 304 and the second gas sensor 306. For example, the first gas sensor 304 and the second gas sensor 306 can be exposed to ambient air that is substantially free of both the ambient gas and the gas analyte for a given time period. The given time period can correspond to a minute, an hour, a day, or the like. The processor 310 can be configured to receive one or more first baseline sensor signals generated by the first gas sensor 304 and one or more second baseline sensor signals generated by the second gas sensor 306 during the given time period.

The processor 310 can further be configured to evaluate a slope of the one or more first baseline sensors signals. For example, the processor 310 can be configured to calculate the slope of each of the one or more first baseline sensors signals and compare the calculated slopes relative to a slope threshold. If the slope of a first baseline sensor signal is equal to or greater than the slope threshold, the first baseline sensor signal can be used for calculating a percent change in resistance in the first gas sensor 304 as described herein.

The processor 310 can further be configured to calculate the percent change in resistance of the first and second gas sensors 304 and 306 by applying a time MA to sensor signals. For example, the processor 310 can further be configured to apply the MA to the one or more first baseline sensor signals having a slope greater than the slope threshold to generate a first MA baseline. N-samples of the one or more first baseline sensor signals can be summed and divided by N to generate the first MA baseline, wherein N is a number of the one or more first baseline sensor signals. The processor 310 can be configured to apply a MA to the one or more second baseline sensors signals to generate a second MA baseline. N-samples of the one or more second baseline sensor signals can be summed and divided by N to generate the second MA baseline, wherein N is a number of the one or more second baseline sensor signals. The first and second MA baselines can be used to compensate for effects that the ambient gas can have on the monitoring system 300.

The first gas sensor 304 can be configured to monitor the gas source 302 during the one or more gas source states. The first gas sensor 304 can be configured to monitor the gas source 302 during the emitting gas state for the gas analyte and generate a monitored sensor signal characterizing an amount of the gas analyte released by the gas source 302 at a given time. The given time can correspond to an instance of time wherein the gas source 302 can be releasing the gas analyte. In the example of the battery, a healthy battery can release substantially no gas analyte, for example, during a charging cycle and/or discharging cycle. As the health of the battery can begin to degrade, the battery can release the gas analyte during the charge cycle and/or discharge cycle. The first gas sensor 304 can be configured to monitor the battery during a cycle condition for the gas analyte and generate a monitored sensor signal characterizing an amount of the gas analyte released by the battery at a given time.

The processor 310 can further be configured to receive the monitored sensor signal. The processor 310 can further be configured to subtract from the first MA baseline the monitored sensor signal to generate a monitored sensor difference. The processor 310 can further be configured to divide the monitored sensor difference by the first MA baseline to determine a percentage change response relative to the first MA baseline. The second gas sensor 306 can be configured to monitor the ambient environment 308 during the emitting gas state for the ambient gas and generate a reference sensor signal characterizing the amount of the ambient gas in the ambient atmosphere 308 at the given time. In the example of the battery, the second gas sensor 306 can be configured to monitor the ambient environment 308 during the charging cycle and/or the discharging cycle. The processor 310 can further be configured to subtract from the second MA baseline the reference sensor signal to generate a reference sensor difference. The processor 310 can further be configured to divide the reference sensor difference by the second MA baseline to determine a percentage change response relative to the second MA baseline.

Accordingly, the processor 310 can be configured to determine a first sensor output (e.g., the monitored sensor difference) based upon a percent change of a first sensor signal (e.g., the monitored sensor signal) relative to a first averaged sensor signal (e.g., the second MA baseline), and a second sensor output (e.g., the reference sensor difference) based upon a percent change of the second sensor signal (e.g., the reference sensor signal) relative to a second averaged sensor signal (the second MA baseline).

The processor 310 can further be configured to subtract the percentage change response relative to the first MA baseline from the percentage change response relative to the second MA baseline to generate an overall difference sensor signal. Thus, the reference gas signal can be used to null out changes in gas concentration common to both the first and second sensors 304 and 306. Accordingly, the ambient gas detected by both the first and second sensors 304 and 306 can be identified by the monitoring system 300. The processor 310 can further be configured to compare the overall difference sensor signal relative to a threshold. The processor 310 can further be configured to generate an alert signal 314 based on a result of the comparison.

For example, the processor 310 can be configured to compare the overall difference sensor signal relative to the threshold to determine if the overall difference sensor signal is equal to or less than the threshold. Alternatively, the processor 310 can be configured to compare the overall difference sensor signal relative to the threshold to determine if the overall difference sensor signal is equal to or greater than the threshold. The processor 310 can be configured to generate the alert signal 314 in response to the overall difference gas signal being equal to or less (or alternatively greater) than the threshold. In one example, the threshold can include one of the sensitivity threshold, the upper-band threshold and the lower band threshold. These thresholds can be determined by the processor 310 according to the methods described herein.

For example, the processor 310 can further be configured to determine the upper band threshold at K times a standard deviation of the one or more first baseline sensor signals above the MA baseline. The processor 106 can further be configured to determine a lower band threshold at K times the standard deviation of the one or more first baseline sensor signals below the MA baseline. The processor 310 can be configured to determine the sensitivity threshold based on the MA of the one or more first baseline sensors signals and a difference value between a minimum sensitivity MS and a reference. The sensitivity threshold can be defined by the following equation: MA*(1−MS), wherein 1 can correspond to the reference.

The processor 310 can further be configured to compare the overall difference sensor signal to one of the sensitivity threshold and the lower band threshold. Alternatively, the processor 310 can be configured to compare the overall difference sensor signal to one of the sensitivity threshold and the upper band threshold. The processor 310 can be configured to generate the alert signal 314 in response to the overall difference sensor signal being equal to or less than one of the sensitivity threshold and the lower band threshold (or being equal to or greater than one of the sensitivity threshold and the upper band threshold).

The alert signal 314 can be transmitted to one or more systems to cause the one or more systems to take one or more preemptive measures as described herein. In the example of the battery, the gas analyte detected during the cycle condition can be interpreted as a warning that the battery can be at risk of thermal runaway. By providing an early warning, fires, explosions and injuries that can be caused in response to a thermal runaway condition can be substantially mitigated. Thus, the monitoring system 300 can detect a thermal runaway condition in a development stage. Accordingly, by detecting a thermal runaway scenario at the development stage, preventive measures can be implemented to prevent hazardous conditions and damage to the battery.

Figure 4:
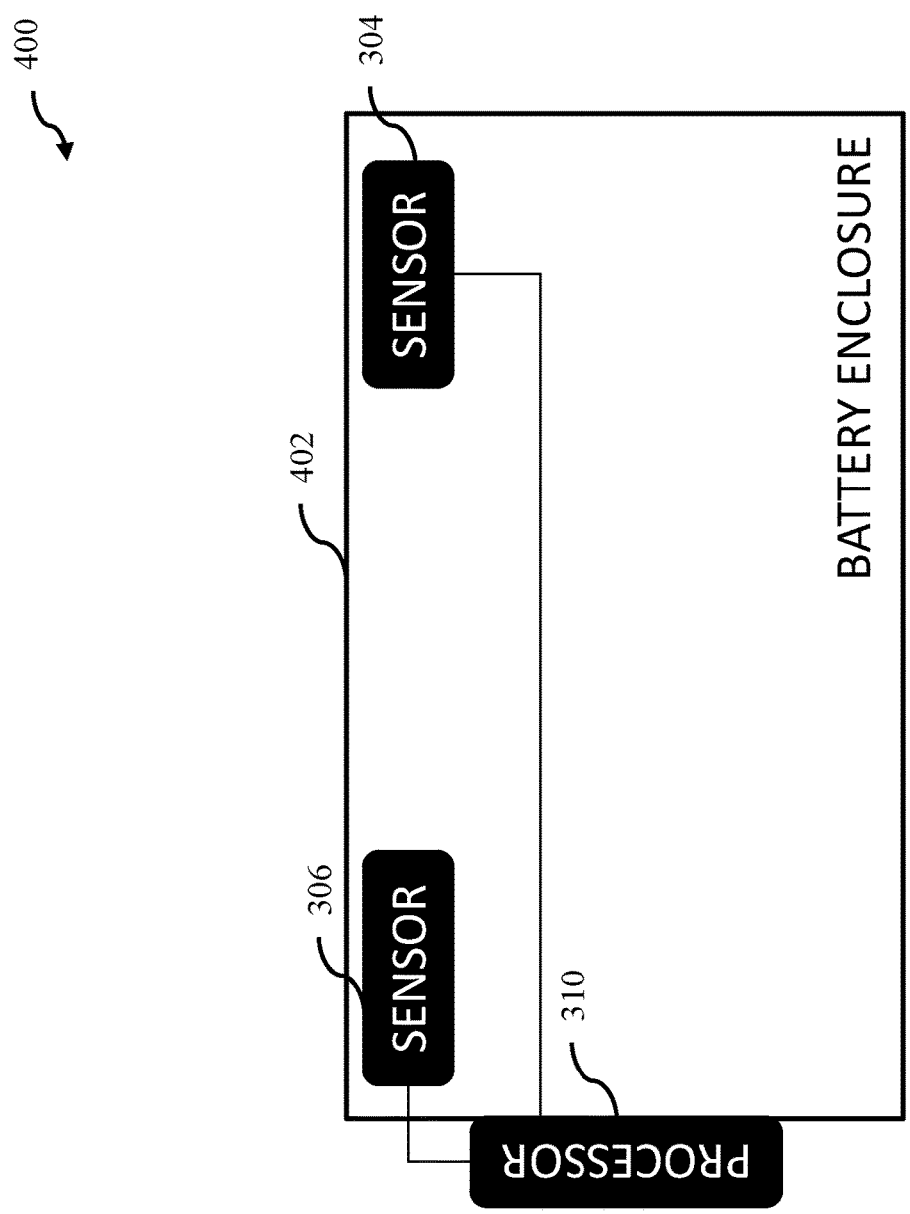
FIG. 4 depicts an example of an enclosure.

The monitoring system 300 can be configured with one or more enclosures. In one example, the enclosure can be a battery enclosure 400, such as depicted in FIG. 4. The battery enclosure 400 can include a housing 402 to house the battery (not depicted in FIG. 4), the first gas sensor 304 and the second gas sensor 306. In FIG. 4, the second gas sensor 406 can be positioned relative to the battery, such that second gas sensor 306 can be substantially free of susceptibility to the gas analyte released by the battery. In an example, the processor 310 can be positioned outside the battery enclosure 400. Alternatively, the processor 310 can be positioned within the battery enclosure 400.

In another example, the enclosure can be a battery enclosure 500, such as depicted in FIG. 5. The battery enclosure 502 can include a housing 502 to house the battery (not depicted in FIG. 5). The battery enclosure 500 can include an intake 504. The intake 504 can be configured to draw ambient air into the housing 502 to cool the battery. The second gas sensor 306 can be positioned within the intake 504. The battery enclosure 500 can further include an exhaust 506. The exhaust 506 can be configured to expel gas in the housing 502 into a surrounding environment. The expelled gas can include the ambient air drawn by the intake 504, the gas analyte emitted by the battery or a mixture thereof. The first gas sensor 304 can be positioned within the exhaust 506. In FIG. 5, the second gas sensor 306 can be positioned relative to the battery such that second gas sensor 306 can be substantially free of susceptibility to the gas analyte released by the battery 02. In an example, the processor 310 can be positioned outside the battery enclosure 500. Alternatively, the processor 310 can be positioned within the battery enclosure 500.

In an even further example, the enclosure can be a lithium-ion battery charging and storage enclosure 600, such as depicted in FIG. 6. The lithium-ion battery charging and storage enclosure 600 can include a housing 602 to house the battery (not depicted in FIG. 6). The battery in this example can correspond to a lithium-ion battery. The lithium-ion battery charging and storage enclosure 600 can include an intake 602. The intake 604 can be configured to draw ambient air into the housing 602 to cool the lithium-ion battery. The second gas sensor 606 can be positioned within the intake 604. The lithium-ion battery charging and storage enclosure 600 can further include an exhaust 606. The exhaust 606 can be configured expel gas in the housing 602 into a surrounding environment. The expelled gas can include the ambient air drawn by the intake 604, the gas analyte emitted by the lithium-ion battery or a mixture thereof. The first gas sensor 604 can be positioned within the exhaust 606. In FIG. 6, the second gas sensor 306 can be positioned relative to the lithium-ion battery such that second gas sensor 306 can be substantially free of susceptibility to the gas analyte released by the lithium-ion battery. In an example, the processor 310 can be positioned outside the lithium-ion battery charging and storage enclosure 600. Alternatively, the processor 310 can be positioned within the lithium-ion battery charging and storage enclosure 600.

Figure 7:
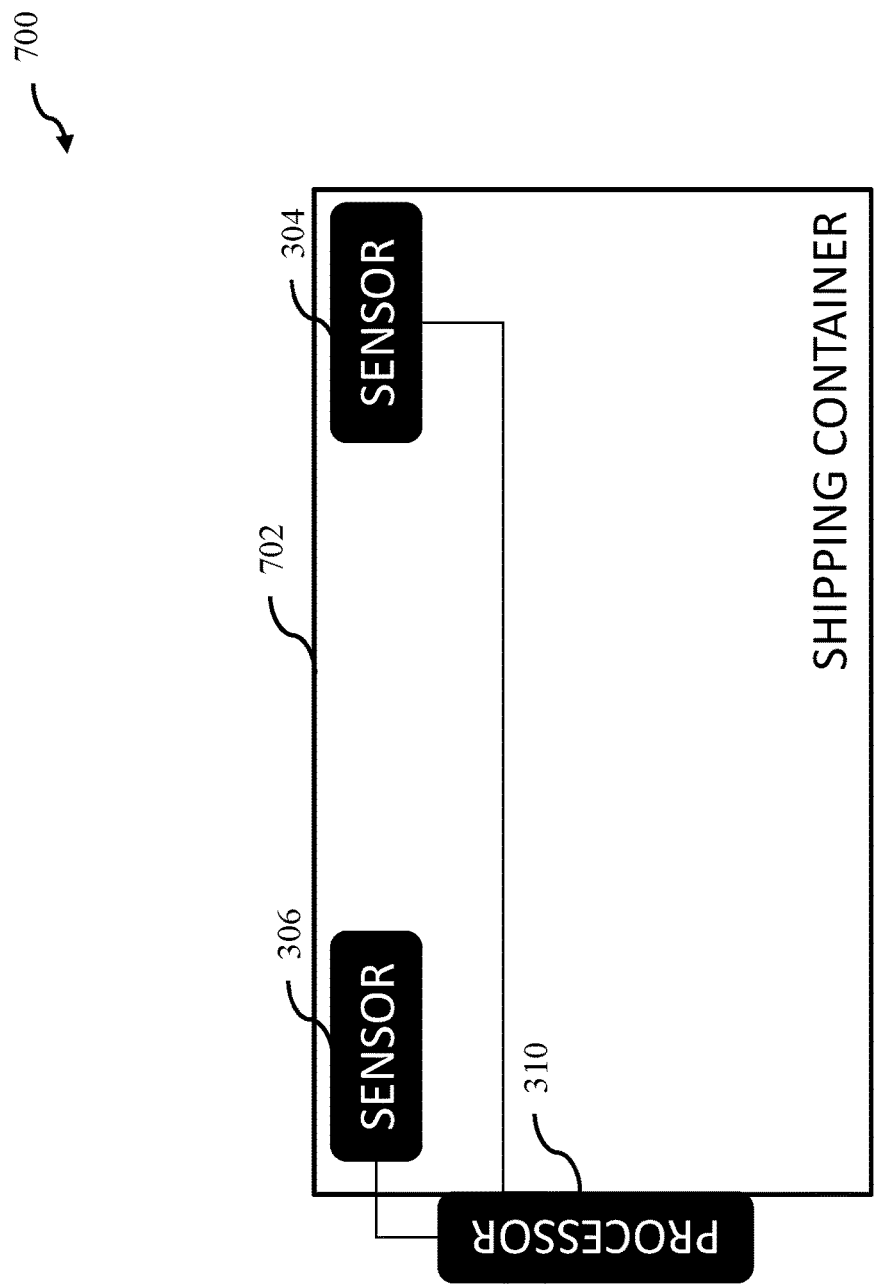
FIG. 7 depicts a further example of an enclosure.

In another example, the battery enclosure can be a shipping container 700, such as depicted in FIG. 7. The shipping container 700 can house the battery (not depicted in FIG. 7), the first gas sensor 304 and the second gas sensor 306. In FIG. 7, the second gas sensor 306 can be positioned relative to the battery such that second gas sensor 306 can be substantially free of susceptibility to the gas analyte released by the battery. In an example, the processor 310 can be positioned outside the shipping container 700. Alternatively, the processor 310 can be positioned within the shipping container 700.

Figure 8:
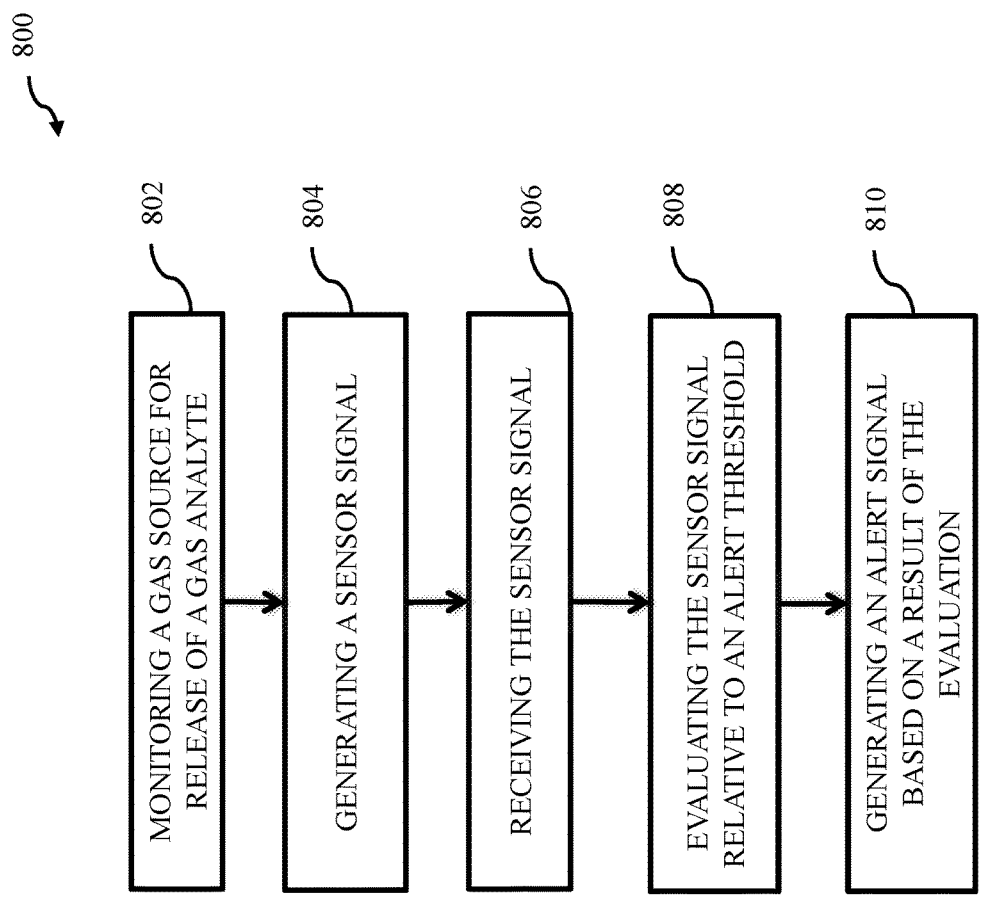
FIG. 8 depicts an example of a flow diagram illustrating an example method for monitoring a gas source for a gas analyte.
Figure 9:
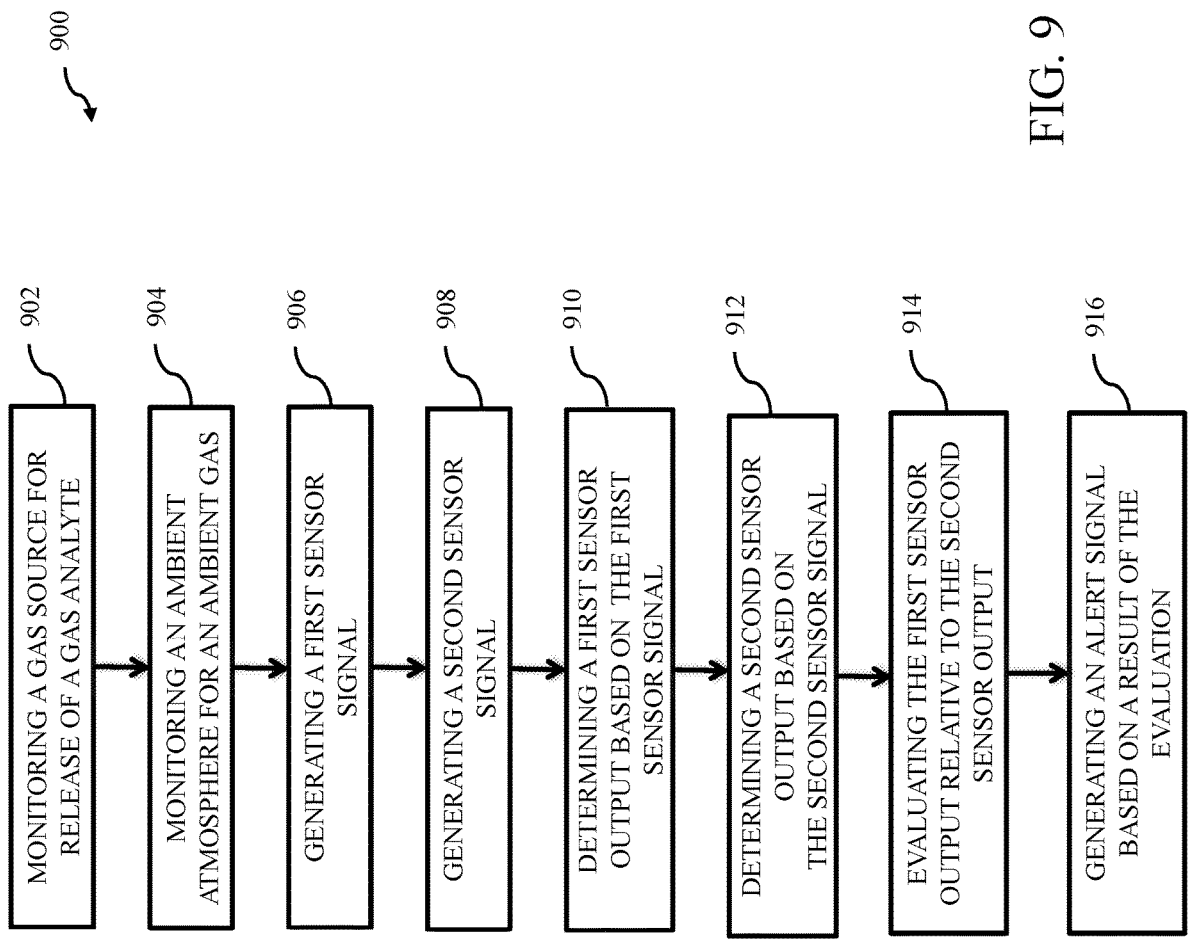
FIG. 9 depicts another example of a flow diagram illustrating an example method for monitoring a gas source for a gas analyte.
Figure 10:
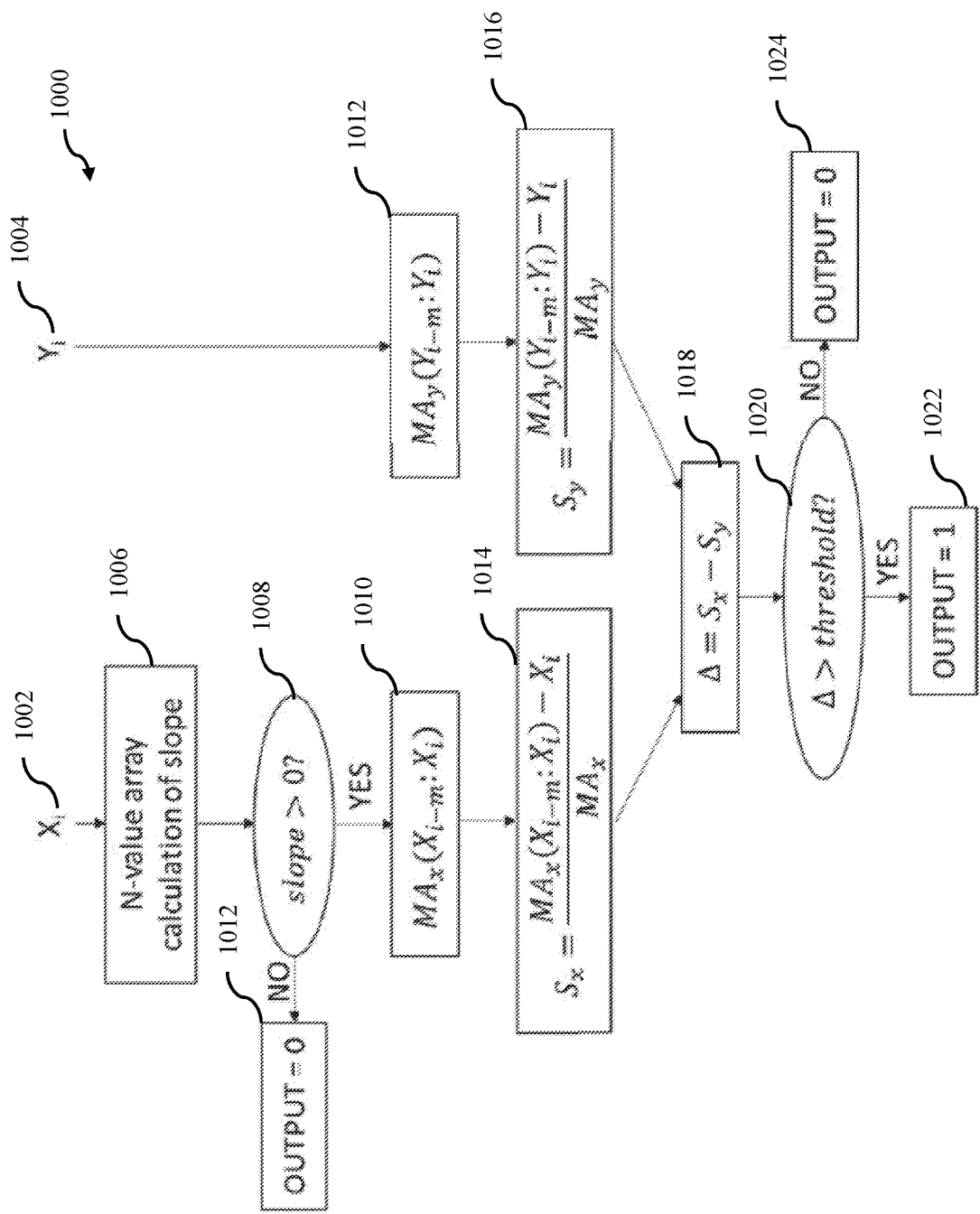
FIG. 10 depicts an even further example of a flow diagram illustrating an example method for monitoring a gas source for a gas analyte.

In view of the foregoing structural and functional features described above, methods that can be implemented will be better appreciated with reference to FIGS. 8-10. While, for purposes of simplicity of explanation, the methods of FIGS. 8-10 are depicted and described as executing serially, it is to be understood and appreciated that such methods are not limited by the illustrated order, as some aspects could, in other embodiments, occur in different orders and/or concurrently with other aspects from that shown and described herein. Moreover, not all illustrated features may be required to implement the methods. The methods or portions thereof can be implemented as instructions stored in one or more non-transitory storage media as well as be executed by a processing resource (e.g., the processor 106, as depicted in FIG. 1 and/or the processor 310, as depicted in FIG. 3).

FIG. 8 depicts an example of a method 800 for monitoring a gas source for a gas analyte. For example, the method 800 can be implemented by the monitoring system 100, as depicted in FIG. 1. The method begins at 802 by monitoring a gas source for a gas analyte. At 804, a sensor signal characterizing an amount of the gas analyte being released by the gas source can be generated. At 806, the sensor signal can be received. At 808, the sensor signal can be evaluated relative to an alert threshold. At 810, an alert signal can be generated based on a result of the evaluation.

FIG. 9 depicts another example of a method 900 for monitoring a gas source for a gas analyte. For example, the method 900 can be implemented by the monitoring system 300, as depicted in FIG. 3. The method begins at 902 by monitoring a gas source for release of a gas analyte. At 904, an ambient environment can be monitored for a presence of an ambient gas. At 906, a first sensor signal characterizing an amount of the gas analyte being released by the gas source can be generated. At 908, a second sensor signal characterizing an amount of the ambient gas present in the ambient environment can be generated. At 910, a first sensor output can be determined based upon a percent change of the first sensor signal relative to a first averaged sensor signal. At 912, a second sensor output can be determined based upon a percent change of the second sensor signal relative to a second averaged sensor signal. At 914, the first sensor output can be evaluated relative to second sensor output. At 916, an alert signal can be generated based on a result of the evaluation.

FIG. 10 depicts an even further example of a method 1000 for monitoring a gas source for a gas analyte. For example, the method 1000 can be implemented by the monitoring system 300, as depicted in FIG. 3. The method begins at 1002, by receiving one or more baseline sensors signals generated by a first gas sensor. At 1004, one or more baseline reference sensor signals generated by a second gas sensor can be received. At 1006, a slope of each of the one or more baseline sensors signals can be evaluated. At 1008, if the slope of a given baseline sensor signal is equal to or greater than the slope threshold, the method can proceed to 1010, otherwise the method can proceed to 1012. At 1012, the given baseline sensor signal can be excluded for further use in the method 1000. At 1010, a MA can be applied to the one or more monitored baseline sensor signals having a slope greater than the slope threshold to generate a first MA baseline. N-samples of the one or more baseline sensor signals can be summed and divided by N to generate the first MA baseline, wherein N is a number of the one or more baseline sensor signals. At 1012, a MA can be applied to the one or more baseline reference sensors signals to generate a second MA baseline. N-samples of the one or more baseline references sensor signals can be summed and divided by N to generate the second MA baseline, wherein N is a number of the one or more baseline reference sensor signals. The first and second MA baselines can be used to compensate for effects that the ambient gas can have on the monitoring system 300.

At 1014, the first gas sensor can be configured to monitor the gas source for the gas analyte and generate a monitored sensor signal characterizing the amount of the gas analyte released by the gas source at a given time, for example, during the given state of the gas source. The given time can correspond to an instance of time wherein the gas source can be releasing the gas analyte. Furthermore, at 1014, the monitored sensor signal can be subtracted from the first MA baseline to generate a monitored sensor difference. Moreover, at 1014, the monitored sensor difference can be divided by the first MA baseline to determine a percentage change response relative to the first MA baseline. At 1016, the second gas sensor can be configured to monitor for an ambient gas in an ambient environment and generate a reference sensor signal characterizing the amount of the ambient gas at the given time, for example during a given state of the gas source. Furthermore, at 1016, the reference sensor signal can be subtracted from the second MA baseline to generate a reference sensor difference. Moreover, at 1016, the reference sensor difference can be divided by the second MA baseline to determine a percentage change response relative to the second MA baseline.

At 1018, the percentage change response relative to the first MA baseline can be subtracted from the percentage change response relative to the second MA baseline to generate an overall difference sensor signal. At 1020, the overall difference sensor signal can be compared relative to an alert threshold. If the overall difference sensor signal is greater than the alert threshold, the method can proceed to 1022, otherwise the method can proceed to 1028. At 1022, an alert (e.g., the alert signal 314, as depicted in FIG. 3) can be generated. At 1028, no alert can be generated. The alert can be transmitted to one or more systems to cause the one or more systems to take one or more preemptive measures as described herein.

It is noted that the terms "substantially" and "about" may be utilized herein to represent an inherent degree of uncertainty that can be attributed to any quantitative comparison, value, measurement, or other representation. These terms are also utilized herein to represent a degree by which a quantitative representation may vary from a stated reference without resulting in a change in the basic function of the subject matter at issue.

While particular examples above have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method comprising:
monitoring a gas analyte using a monitoring system capable of monitoring lithium ion battery off-gas, wherein the gas analyte comprises a lithium ion battery electrolyte material released by one or more lithium ion batteries;
generating a sensor signal characterizing an amount of the gas analyte;
receiving the sensor signal;
evaluating the sensor signal relative to a threshold, wherein the sensor signal is generated during a first state of the one or more lithium ion batteries, the first state corresponding to a state wherein the one or more lithium ion batteries are releasing the gas analyte;
generating one or more baseline sensor signals characterizing an amount of the gas analyte being released during a second state of the one or more lithium ion batteries, the second state corresponding to a state wherein the one or more lithium ion batteries are not releasing the gas analyte; and
generating an alert signal based on a result of the evaluation.

2. The method of claim 1, further comprising applying a moving average (MA) to the one or more baseline sensor signals to determine a MA threshold.

3. The method of claim 1,
wherein the gas analyte comprises a lithium ion battery electrolyte gas comprising a volatile electrolyte solvent and/or a volatile component of an electrolyte mixture of the one or more lithium batteries, wherein the gas analyte comprises a volatile organic compound, and wherein the volatile organic compound comprises one or more of diethyl carbonate, dimethyl carbonate, methyl ethyl carbonate, ethylene carbonate, propylene carbonate, and vinylene carbonate.

4. The method of claim 1, wherein the gas analyte comprises one or more gases released by the one or more lithium ion batteries, the gases comprising one of more of carbon dioxide, carbon monoxide, methane, ethane, hydrogen, oxygen, nitrogen oxides, volatile organic compounds, hydrogen sulfide, sulfur oxides, ammonia, chlorine, propane, ozone, ethanol, hydrocarbons, hydrogen cyanide, combustible gases, flammable gases, toxic gases, corrosive gases, oxidizing gases, and reducing gases.

5. The method of claim 2, further comprising determining an upper band threshold at K times a standard deviation of the one or more baseline sensor signals above the MA threshold, the threshold corresponding to the upper band threshold.

6. The method of claim 2, further comprising determining a lower band threshold at K times the standard deviation of the one or more baseline sensor signals below the MA threshold, the threshold corresponding to the lower band threshold.

7. The method of claim 2, further comprising
determining a given band threshold at K times the standard deviation of the one or more baseline sensor signals one of above and below the MA threshold;
determining a sensitivity threshold based on the MA threshold and a difference value between a minimum sensitivity and a reference;
comparing the sensitivity threshold relative to the given band to identify a threshold having a greatest value; and
wherein the evaluating comprises evaluating the sensor signals relative the threshold having the greatest value.

8. A system comprising:
a monitoring system capable of monitoring lithium ion battery off-gas, comprising:
a gas sensor configured to monitor for a gas analyte comprising a lithium ion battery electrolyte material released by one or more lithium ion batteries;
a memory to store machine readable instructions;
a processor to access the memory and execute the machine readable instructions, the machine readable instructions causing the processor to:
receive a sensor signal generated by the gas sensor characterizing an amount of the gas analyte;
evaluate the sensor signal relative to a threshold; and
generate an alert signal based on a result of the evaluation, wherein the sensor signal is generated during a first state of the one or more lithium ion batteries, the first state corresponding to a state wherein the one or more lithium ion batteries are releasing the gas analyte; and wherein the machine-readable instructions further cause the processor to generate one or more baseline sensor signals characterizing an amount of the gas analyte being released during a second state of the one or more lithium ion batteries, the second state corresponding to a state wherein the one or more lithium ion batteries are not releasing the gas analyte.

9. The system of claim 8, wherein the machine-readable instructions further cause the processor to apply a moving average (MA) to the one or more baseline sensor signals to determine a MA threshold.

10. The system of claim 8, comprising an enclosure configured to house the one or more lithium ion batteries.

11. The system of claim 8, wherein the gas sensor comprises a chemi-resistive sensor.

12. The system of claim 8, wherein the monitoring system is configured to monitor lithium ion battery off-gas to detect a thermal runaway condition in a development stage to avoid thermal runaway.

13. The system of claim 8, wherein the gas analyte comprises a lithium ion battery electrolyte gas comprising a volatile electrolyte solvent and/or a volatile component of an electrolyte mixture of the one or more lithium ion batteries.

14. The system of claim 8, wherein the gas analyte comprises one or more gases released by the one or more lithium ion batteries, the gases comprising one or more of carbon dioxide, carbon monoxide, methane, ethane, hydrogen, oxygen, nitrogen oxides, volatile organic compounds, hydrogen sulfide, sulfur oxides, ammonia, chlorine, propane, ozone, ethanol, hydrocarbons, hydrogen cyanide, combustible gases, flammable gases, toxic gases, corrosive gases, oxidizing gases, and reducing gases.

15. The system of claim 9, wherein the machine-readable instructions further cause the processor to determine an upper band threshold at K times a standard deviation of the one or more baseline sensor signals above the MA threshold, the threshold corresponding to the upper band threshold.

16. The system of claim 9, wherein the machine-readable instructions further cause the processor to determine a lower band threshold at K times the standard deviation of the one or more baseline sensor signals below the MA threshold, the threshold corresponding to the lower band threshold.

17. The system of claim 9, wherein the system is further configured to:

determine a given band threshold at K times the standard deviation of the one or more baseline sensor signals one of above and below the MA threshold;

determine a sensitivity threshold based on the MA threshold and a difference value between a minimum sensitivity and a reference; and compare the sensitivity threshold relative to the given band to identify a threshold having a greatest value, wherein the evaluating comprises evaluating the sensor signals relative the threshold having the greatest value.

18. The system of claim 10, wherein the gas sensor is located within the enclosure.

19. The system of claim 11, wherein the chemi-resistive sensor is capable of measuring the gas analyte in parts-per-million (ppm).

20. The system of claim 13, wherein the gas analyte comprises a volatile organic compound.

21. The system of claim 20, wherein the volatile organic compound comprises one or more of diethyl carbonate, dimethyl carbonate, methyl ethyl carbonate, ethylene carbonate, propylene carbonate, vinylene carbonate, or a combination thereof.

22. A method comprising:
monitoring a gas analyte using a monitoring system capable of monitoring lithium ion battery off-gas;
generating a first sensor signal characterizing an amount of the gas analyte comprising one or more gases released by the one or more lithium ion batteries, the gases comprising one or more of carbon dioxide, carbon monoxide, methane, ethane, hydrogen, oxygen, nitrogen oxides, volatile organic compounds, hydrogen sulfide, sulfur oxides, ammonia, chlorine, propane, ozone, ethanol, hydrocarbons, hydrogen cyanide, combustible gases, flammable gases, toxic gases, corrosive gases, oxidizing gases, and reducing gases;
monitoring an ambient environment for an ambient gas, wherein the ambient environment is substantially free of the gas analyte;
generating a second sensor signal characterizing an amount of the ambient gas present in the ambient atmosphere;
determining a first sensor output based upon a percent change of the first sensor signal relative to a first averaged sensor signal;
determining a second sensor output based upon a percent change of the second sensor signal relative to a second averaged sensor signal;
evaluating the first sensor output relative to the second sensor output; and
generating an alert signal based on a result of the evaluation.

23. The method of claim 22, further comprising
receiving one or more monitored baseline sensors signals characterizing an amount of a gas in the ambient environment generated at a first gas sensor during a given time period,
receiving one or more reference baseline sensors signals characterizing an amount of a gas in the ambient environment generated at a second gas sensor during the given time period, wherein the ambient environment during the given time period is substantially free of the gas analyte.

24. The method of claim 22, further comprising:
evaluating a slope of the one or more monitored baseline sensor signals relative to a slope threshold;

applying a moving average (MA) to the one or more monitored baseline sensor signals having a slope greater than the slope threshold to generate a first MA baseline; and applying the MA to the one or more baseline reference sensors signals to generate a second MA baseline;

wherein determining the first sensor output based upon the percent change of the first sensor signal relative to the first averaged sensor signal comprises determining a percentage change response relative to the first MA baseline based on a monitored sensor difference between the first sensor signal and the first MA baseline, and further based on the first MA baseline; and wherein determining the second sensor output based upon the percent change of the second sensor signal relative to the second averaged sensor signal comprises determining a percentage change response relative to the second MA baseline based on a reference sensor difference between the second sensor signal and the second MA baseline, and further based on the second MA baseline.

25. The method of claim 23, wherein evaluating the first sensor output relative to the second sensor output comprises:
generating an overall difference sensor signal based on a difference between the percentage change response relative to the first MA baseline and the percentage change response relative to the second MA baseline; and
comparing the overall difference sensor signal relative to a threshold; and
wherein generating the alert signal based on the result of the evaluation comprises generating the alert signal based on a result of the comparison.

26. A system comprising:
a monitoring system capable of monitoring lithium ion battery off-gas, comprising:
a first gas sensor configured to monitor for a gas analyte, wherein the gas analyte comprises one or more gases released by one or more lithium ion batteries, the gases comprising one or more of carbon dioxide, carbon monoxide, methane, ethane, hydrogen, oxygen, nitrogen oxides, volatile organic compounds, hydrogen sulfide, sulfur oxides, ammonia, chlorine, propane, ozone, ethanol, hydrocarbons, hydrogen cyanide, combustible gases, flammable gases, toxic gases, corrosive gases, oxidizing gases, and reducing gases;
a second gas sensor configured to monitor an ambient environment for ambient gas, wherein the ambient environment is substantially free of the gas analyte;
a memory to store machine readable instructions;
a processor to access the memory and execute the machine readable instructions, the machine readable instructions causing the processor to:
receive a first sensor signal characterizing an amount of the gas analyte;
receive a second sensor signal characterizing an amount of the ambient gas present in the ambient atmosphere;
determine a first sensor output based upon a percent change of the first sensor signal relative to a first averaged sensor signal;
determine a second sensor output based upon a percent change of the second sensor signal relative to a second averaged sensor signal;
evaluate the first sensor output relative to the second sensor output; and generate an alert signal based on a result of the evaluation.

\* \* \* \* \*

UNITED STATES PATENT AND TRADEMARK OFFICE
CERTIFICATE OF CORRECTION

PATENT NO. : 10,877,011 B2
APPLICATION NO. : 15/637381
DATED : December 29, 2020
INVENTOR(S) : Stephen Randall Cummings et al.

Page 1 of 1

It is certified that error appears in the above-identified patent and that said Letters Patent is hereby corrected as shown below:

On the Title Page

Item (73) Assignee: please delete "Nexceris, LLC" and insert --NEXCERIS INNOVATION HOLDINGS, LLC--

Signed and Sealed this
First Day of June, 2021

Drew Hirshfeld
*Performing the Functions and Duties of the*
*Under Secretary of Commerce for Intellectual Property and*
*Director of the United States Patent and Trademark Office*